(12) United States Patent
Govari

(10) Patent No.: US 11,064,920 B2
(45) Date of Patent: Jul. 20, 2021

(54) BRAIN CLOT CHARACTERIZATION USING OPTICAL SIGNAL ANALYSIS, AND CORRESPONDING STENT SELECTION

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 319 days.

(21) Appl. No.: 16/057,189

(22) Filed: Aug. 7, 2018

(65) Prior Publication Data

US 2020/0046267 A1    Feb. 13, 2020

(51) Int. Cl.
| | | |
|---|---|---|
| *A61B 5/1459* | (2006.01) | |
| *A61B 1/07* | (2006.01) | |
| *A61B 5/06* | (2006.01) | |
| *A61B 5/145* | (2006.01) | |
| *A61B 5/00* | (2006.01) | |
| *A61B 17/22* | (2006.01) | |
| *A61B 17/00* | (2006.01) | |

(52) U.S. Cl.
CPC .............. *A61B 5/1459* (2013.01); *A61B 1/07* (2013.01); *A61B 5/062* (2013.01); *A61B 5/14535* (2013.01); *A61B 5/4064* (2013.01); *A61B 5/4836* (2013.01); *A61B 5/6876* (2013.01); *A61B 17/22* (2013.01); *A61B 2017/00057* (2013.01)

(58) Field of Classification Search
None
See application file for complete search history.

(56) References Cited

U.S. PATENT DOCUMENTS

| | | |
|---|---|---|
| 4,900,303 A | 2/1990 | Lemelson |
| 5,938,595 A | 8/1999 | Glass et al. |
| 2003/0191398 A1 | 10/2003 | Motz et al. |
| 2004/0073120 A1 | 4/2004 | Motz et al. |
| 2005/0215946 A1 | 9/2005 | Hansmann et al. |
| 2007/0093703 A1 | 4/2007 | Sievert et al. |

(Continued)

FOREIGN PATENT DOCUMENTS

| | | | |
|---|---|---|---|
| WO | WO-2017216645 A2 * | 12/2017 | ......... A61B 18/1477 |
| WO | 2018137949 A1 | 2/2018 | |

OTHER PUBLICATIONS

EP 19190265.9-1132—Extended European Search Report dated Dec. 6, 2019.

(Continued)

*Primary Examiner* — Eric F Winakur
*Assistant Examiner* — Marjan Fardanesh
(74) *Attorney, Agent, or Firm* — Troutman Pepper Hamilton Sanders LLP

(57) ABSTRACT

A medical system includes a probe, an electrooptical measurement unit, and a processor. The probe, which is configured for insertion into a blood vessel of a brain, includes one or more optical fibers configured to guide an optical signal to interact with a brain clot in the blood vessel, and to output the optical signal that interacted with the brain clot. The electrooptical measurement unit is configured to collect and measure the outputted optical signal. The processor is configured to identify a composition of the brain clot by analyzing the measured optical signal from the probe.

13 Claims, 4 Drawing Sheets

(56) References Cited

U.S. PATENT DOCUMENTS

| | | | |
|---|---|---|---|
| 2008/0013900 A1* | 1/2008 | Harris | A61B 1/07 385/117 |
| 2008/0300493 A1* | 12/2008 | Gatto | A61B 90/36 600/479 |
| 2011/0152752 A1 | 6/2011 | Dacey et al. | |
| 2012/0022360 A1 | 1/2012 | Kemp | |
| 2012/0007811 A1 | 3/2012 | Okada | |
| 2014/0018005 A1 | 6/2014 | Hoseit | |

OTHER PUBLICATIONS

Pending U.S. Appl. No. 62/675,952, filed May 24, 2018.
Pending U.S. Appl. No. 15/674,380, filed Aug. 17, 2017.

* cited by examiner

BRAIN CLOT CHARACTERIZATION USING OPTICAL SIGNAL ANALYSIS, AND CORRESPONDING STENT SELECTION

FIELD OF THE INVENTION

The present invention relates generally to medical probes, and particularly to catheters for cerebrovascular applications.

BACKGROUND OF THE INVENTION

Various types of catheters include optical elements. For example, U.S. Patent Application Publication 2005/0215946 describes a method for making a plurality of measurements at a treatment site in a patient's vasculature with a sensor positioned on a neurovascular catheter. The sensor is used for sensing a vascular obstruction at the treatment site, and selecting a treatment parameter based, at least in part, upon a sensed property of the obstruction, and treating the obstruction to reduce the blockage. In some embodiments, a fiber optic sensor comprises a sensor element, which is configured to be inserted into the utility lumen, is used, for example, to evaluate a chemical marker of ischemia. The fiber optic sensor may include one or more fiber optic fibers, which operatively connect the sensor element to a detector via a cable. The sensor may be configured such that the sensor element can be extended past the distal end of the catheter. In modified embodiments, a fiber optic sensor or portions thereof may be integrated into the body of the catheter.

As another example, U.S. Patent Application Publication 2011/0152752 describes systems, devices, methods, and compositions for providing an actively-controllable disinfecting implantable device configured to, for example, treat or prevent an infection in a biological subject. In an embodiment, a catheter device is positioned to provide vascular access. In an embodiment, the system includes, among other parts, at least one catheter device including one or more energy waveguides such as an optical fiber.

U.S. Patent Application Publication 2004/0073120 describes a system and method for using spectroscopy, for example, Raman spectroscopy for diagnosis of tissue conditions such as vascular disease or cancer. A system is provided for measuring tissue includes a fiber optic probe having a proximal end, a distal end, and a diameter of 2 mm or less. This small diameter allows the system to be used for the diagnosis of coronary artery disease or other small lumens or soft tissue with minimal trauma. A delivery optical fiber is included in the probe coupled at the proximal end to a light source. A filter for the delivery fibers is included at the distal end. The system includes a collection optical fiber (or fibers) in the probe that collects Raman scattered radiation from tissue, the collection optical fiber is coupled at the proximal end to a detector. A second filter is disposed at the distal end of the collection fibers.

U.S. Patent Application Publication 2007/0093703 describes a catheter that has an elongated catheter shaft adapted for introduction into a body passageway of a patient. At least one optical fiber extends through the catheter shaft. The optical fiber has a distal end positioned at or near a distal end of the catheter for illuminating tissue and receiving light energy from tissue at the location of the distal end of the tip. A distal region of the catheter includes a deformed portion having a crest offset from a longitudinal axis of the catheter shaft. A distal tip of the optical fiber is positioned at the crest to increases the likelihood of the distal tip contacting tissue of a wall of the body passageway.

SUMMARY OF THE INVENTION

An embodiment of the present invention provides a medical system including a probe, an electrooptical measurement unit, and a processor. The probe, which is configured for insertion into a blood vessel of a brain, includes one or more optical fibers configured to guide an optical signal to interact with a brain clot in the blood vessel, and to output the optical signal that interacted with the brain clot. The electrooptical measurement unit is configured to collect and measure the outputted optical signal. The processor is configured to identify a composition of the brain clot by analyzing the measured optical signal from the probe.

In some embodiments, the processor is configured to identify the composition of the brain clot based on an intensity of the measured optical signal.

In some embodiments, the optical signal includes monochromatic red light.

In an embodiment, the system further includes an optical sensor fitted at a distal end of at least one of the one or more optical fibers.

In another embodiment, the optical sensor includes a Bragg grating sensor configured to reflect a monochromatic red light.

In some embodiments, the one or more optical fibers are configured to guide the optical signal to be transmitted via the brain clot, or to be reflected from the brain clot.

In some embodiments, the processor is configured to identify, based on the measured optical signal, whether the composition of the brain clot is characterized by red blood cells or by white blood cells.

In an embodiment, the processor is configured to output a recommendation for selecting a brain-clot removal device that matches the composition of the brain clot.

In another embodiment, the system further includes a clot removal device fitted at a distal end of the probe. There is additionally provided, in accordance with an embodiment of the present invention, a medical method, including guiding an optical signal via one or more optical fibers in a probe that is inserted into a blood vessel of a brain, to interact with a brain clot in the blood vessel. An outputted optical signal that interacted with the brain clot is collected from the probe and measured. A composition of the brain clot is identified by analyzing, in a processor, the measured optical signal from the probe.

The present invention will be more fully understood from the following detailed description of the embodiments thereof, taken together with the drawings in which:

DETAILED DESCRIPTION OF EMBODIMENTS

Overview

Figure 1A:
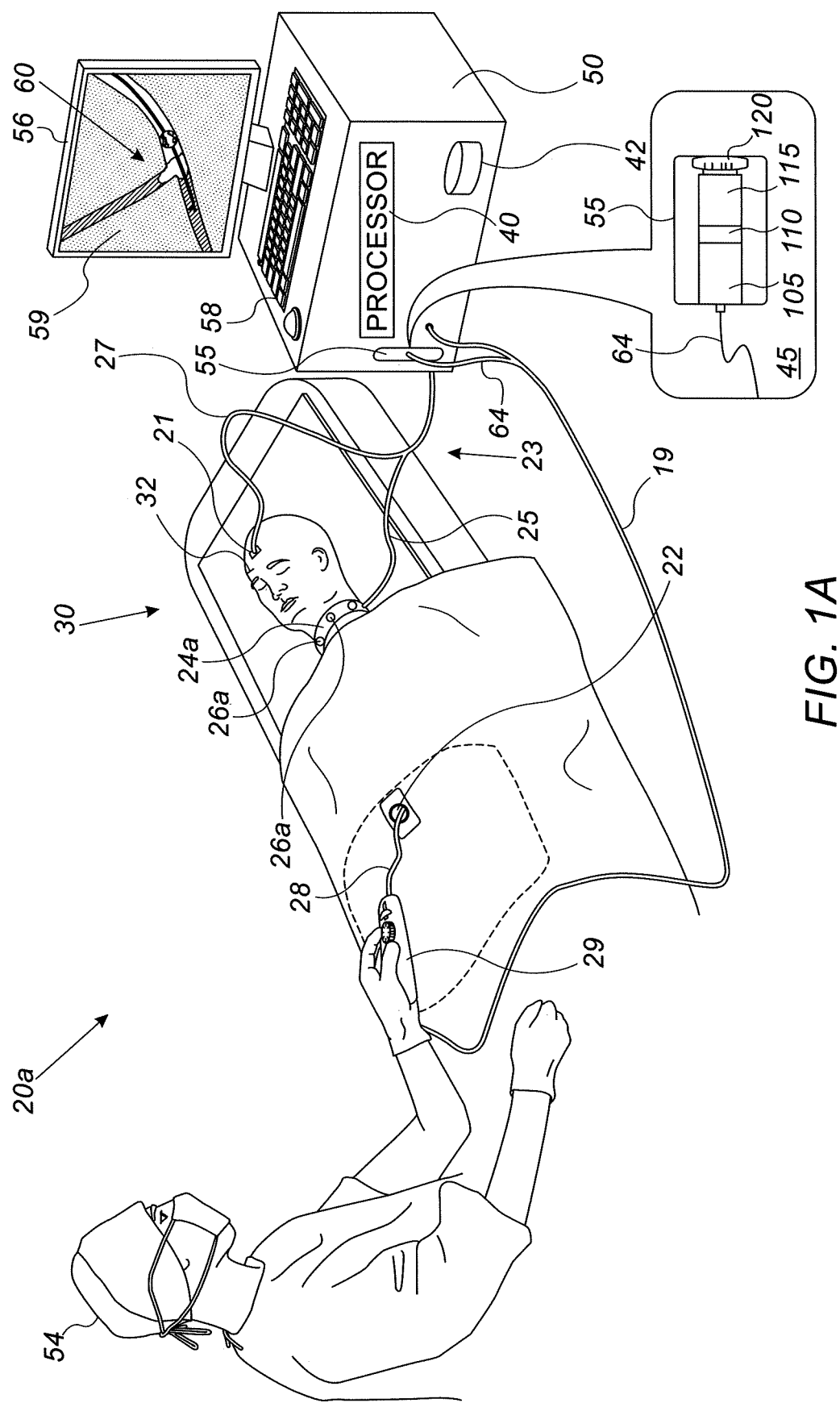
FIGS. 1A and 1B are schematic, pictorial illustrations of catheter-based clot composition analysis and removal systems, in accordance with embodiments of the present invention.

An obstructing clot in a large blood vessel of the brain is a medical emergency condition. The location of the clot in the brain may be detected with computerized tomography (CT) or fluoroscopy imaging, using injection of a contrast agent. A physician may then insert and advance a probe, such as a catheter, fitted with a clot removal device, such as a clot removing stent, into the blood vessel of the brain, and use the stent to attempt to retrieve the imaged clot, so as to remove the obstruction to the flow of blood.

CT and fluoroscopy imaging, however, typically cannot identify the composition of a clot. Clot composition may vary, for example, from a preponderance of red blood cells (typically making the clot relatively solid and hard) to a preponderance of white blood cells (typically making the clot relatively gel-like and pliable). Successful removal of a clot may depend on selecting a stent type that is most suitable for engaging a specific clot composition. Therefore, it is important to analyze clot composition before attempting its removal.

In the context of the present patent application and in the claims, the term "composition of a clot" refers to various chemical, biological and/or physical characteristics of the clot and/or the elements making-up the clot.

Embodiments of the present invention that are described hereinafter provide a system and method for the analysis and identification of the composition of a brain clot to indicate clot characteristics (e.g., solid and hard or gel-like and pliable), and to assist a physician in selecting an optimal clot-removal device.

In some embodiments, an optical fiber is incorporated into a sheath of a catheter to guide an optical signal to interact with the composition of a clot. The optical fiber is coupled at its proximal end to an electrooptical measurement unit, which collects and measures the optical signal that has interacted with the clot, and that the fiber outputted, digitizes the measured signal, and outputs the digital signal to a processor which analyzes the digital signal to identify the composition of the clot. In some embodiments, the processor is further configured to output a recommendation for selecting a brain-clot removal device that matches the composition of the brain clot.

In some embodiments, a distal end of the sheath, which includes the optical fiber, is configured to traverse the clot and allow monochromatic light that propagates in the fiber to interact with the clot composition, which, for instance, results in the propagating light being partially absorbed by the surrounding clot. In this way, a clot comprising a preponderance of white blood cells, for example, absorbs more red light and thus attenuates more of a red-light signal than a clot comprising a preponderance of red blood cells, as further explained below. In such a case, the processor can determine the clot type based on the optical attenuation characteristics of the red light.

In an embodiment, two optical fibers are used, where one fiber guides an incident light and the other fiber collects and guides light transmitted after interacting with the clot composition. The processor then determines the clot type based its optical transmission characteristics.

In some embodiments, an optical source of monochromatic red light at a wavelength of 650 nm is used, which propagates through the clot. The electrooptical measurement unit collects the 650 nm light after being partially absorbed by the surrounding clot. The subsequent measurement and analysis of the relative intensity of the light (e.g., a ratio of reflected to incident light intensities) provides information about whether the clot comprises a preponderance of red blood cells or white blood cells.

In some embodiments, a wavelength-specific reflector, such as a fiber Bragg grating designed with a band-stop window centered at a diagnostic wavelength, is patterned on the distal end of the fiber that is advanced to traverse the clot. In this way, the incident light is selectively reflected at the diagnostic wavelength after interacting with the clot composition, and hence double-passes the clot before being coupled into the electrooptical measurement unit for analysis. Double-passing typically enhances the diagnostic optical signal. For example, passing through the clot twice squares an optical attenuation signal at a diagnostic red wavelength of 650 nm relative to that achieved with a single pass.

In an embodiment, the processor analyzes signals that electrooptical measurement unit spectroscopically measured at several distinct absorption lines in a spectrum of either reflected, or transmitted, wideband optical signals. Based on the multi-wavelength signal, the processor identifies a composition of the clot, as further elaborated below.

As noted above, an indication of the nature of the clot may enable a physician to decide which stent type to use, so as to increase the probability of capturing and fully removing the clot from the blood vessel. Therefore, the disclosed system and method for analyzing clot composition may improve the clinical outcome of a medical emergency catheterization procedure for the removal of a brain clot.

System Description

Figure 1B:
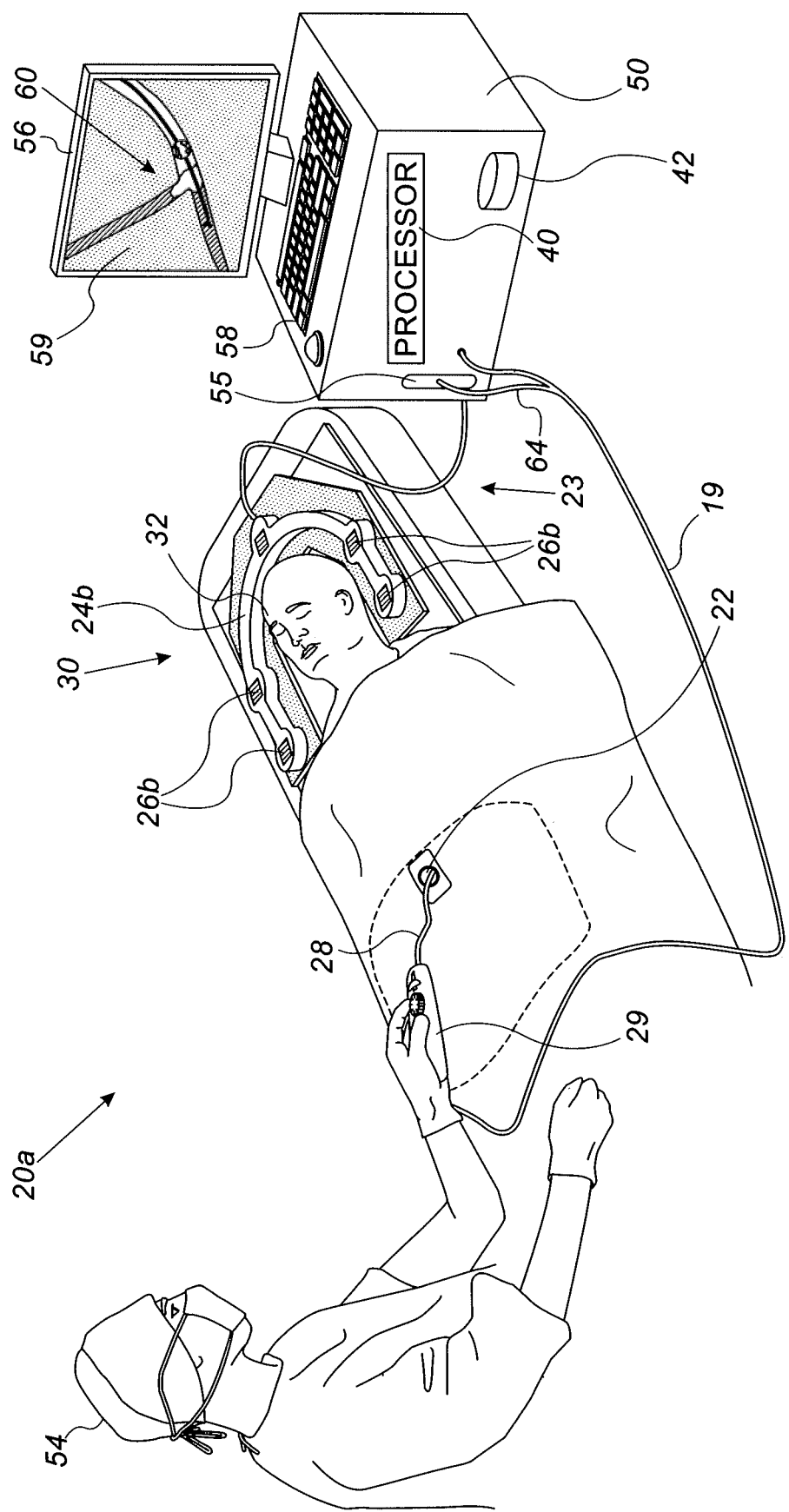

FIGS. 1A and 1B are schematic, pictorial illustrations of catheter-based clot composition analysis and removal systems 20a and 20b, in accordance with embodiments of the present invention.

In some embodiments, prior to performing the catherization procedure, CT images of a patient 22 are acquired. The CT images are stored in a memory 42 for subsequent retrieval by a processor 40. The processor uses the images to present, for example, brain section image 59 demonstrating a clot on a display 56. In another embodiment, during the disclosed catheterization, procedure systems 20a and 20b register a position of a distal end of a catheter 28 inside the patient's brain, with frames of reference of brain images of patient 32, herein assumed by way of example to comprise real-time fluoroscopic images. The position of a catheter distal end is tracked using a magnetic tracking sub-system 23, which tracks spatial coordinates of a magnetic sensor fitted at the distal end.

Using magnetic position tracking sub-system 23, a physician 54 advances the distal end of catheter 28 through blood vessels, usually arteries, to the clot so as to enable diagnosis of the type of clot and optionally to perform a corresponding invasive therapeutic procedure to remove the clot.

In system 20a, shown in FIG. 1A, a location pad 24a, comprised of magnetic tracking sub-system 23, is implemented as a collar put around the neck of patient 32. By putting location pad 24a over the neck, location pad 24a is configured to automatically compensate for patient head movement. Location pad 24a comprises magnetic field radiators 26a which are fixed in position relative to the head of patient 32 and which transmit alternating sinusoidal magnetic fields into a region 30 where the head of patient 32 is located. A console 50 electrically drives radiators 26a via a cable 25. In an embodiment, further compensation of head motion is provided by attaching a reference sensor 21 to the patient's forehead. Console 50 is configured to receive signals from reference sensor 21 via a cable 27. A location tracking system that comprises a neck collar location pad is described in U.S. Provisional Patent Application 62/675, 952, filed May 24, 2018, entitled "Position Sensor on Brain Clot Sheath and Location Pad Collar," which is assigned to the assignee of the present patent application and whose disclosure is incorporated herein by reference.

Physician 54, operating system 20a, holds catheter controller handle 29, which is connected to the proximal end of catheter 28. Controller 29 allows the physician to advance and navigate catheter 28 in the brain, for example through an entry point 22 at an artery at a thigh of patient 32. As noted above and described below, Physician 54 navigates the distal end of catheter 28 using position signals from a magnetic position sensor fitted at the distal end of catheter 28. Console 50 receives the position signals via a cable 19 that connects to catheter 28 via handle 29.

Elements of system 20a, including radiators 26a, are controlled by a system processor 40, comprising a processing unit communicating with one or more memories. Processor 40 may be mounted in console 50, which comprises operating controls 58 that typically include a keypad and/or a pointing device such as a mouse or trackball. Physician 54 uses operating controls on handle 29 to interact with the processor while performing the registration of system 20a. During the registration process, an image 59 of a brain section is presented on display 56. Subsequent to the registration process described above, physician 54 uses the operating controls to advance the distal end of catheter 28 to a brain location 60 where a clot is blocking an artery. The processor presents results of the catheter tracking procedure on display 56.

Processor 40 uses software stored in a memory 42 to operate system 20a. The software may be downloaded to processor 40 in electronic form, over a network, for example, or it may, alternatively or additionally, be provided and/or stored on non-transitory tangible media, such as magnetic, optical, or electronic memory.

In some embodiments of the present invention, an electrooptical measurement unit 55 is included in console 50. Electrooptical measurement unit 55 is configured to collect and measure an optical signal outputted from a fiber optic 64, which is included in catheter 28, as described below, and runs in cable 19 to console 50. Electrooptical measurement unit 55 then conveys the measured signal to processor 40. Based on analyzing the measured signal, processor 40 identifies the composition of a clot, as further elaborated below. In some embodiments, the processor presents the identified clot composition on display 56.

In some embodiments, as seen in an inset 45, electrooptical measurement unit 55 comprises an optical coupler 105, which includes a monochromatic light source (not shown), such as a LED or a laser-diode, to illuminate the clot with monochromatic red light. For clot illumination, coupler 105 couples the light source into a proximal edge of optical fiber 64. Coupler 105 is further configured to couple to a detector 110 an optical signal which fiber 64 outputs (i.e., light that interacted the clot). Detector 110 converts the coupled outputted optical signal into an electrical analog signal. An analog-to-digital conversion circuit 115 digitizes the analog signal and a connector 120 conveys the digitized signal to processor 40 for analysis. In an embodiment connector 120 is further configured to connect electrooptical measurement unit 55 to electrical supply.

System 20b, shown in FIG. 1B, has a different magnetic location pad design, namely a location pad 24b. As seen, location pad 24b is fixed to the bed, and irradiators 26b surround a patient headrest horizontally. In this example, system 20b lacks reference sensor 21, and therefore the head of the patient must be harnessed to keep it motionless. Other components of system 20b are generally identical to those of system 20a. A location tracking system using a location pad similar to location pad 24b is described in U.S. patent application Ser. No. 15/674,380, filed Aug. 10, 2017, entitled "ENT Image Registration," which is assigned to the assignee of the present patent application and whose disclosure is incorporated herein by reference.

Systems 20a and 20b shown in FIGS. 1A and 1B are chosen purely for the sake of conceptual clarity. Other system elements may be included, for example additional controls on handle 29 for controlling the diagnostic tooling designed to determine clot type. CARTO® magnetic tracking systems, which track a location and orientation of a magnetic position sensor in an organ of a body using techniques similar to those applied by systems 20a and 20b, are produced by Biosense-Webster, Irvine, Calif.

Figure 2:
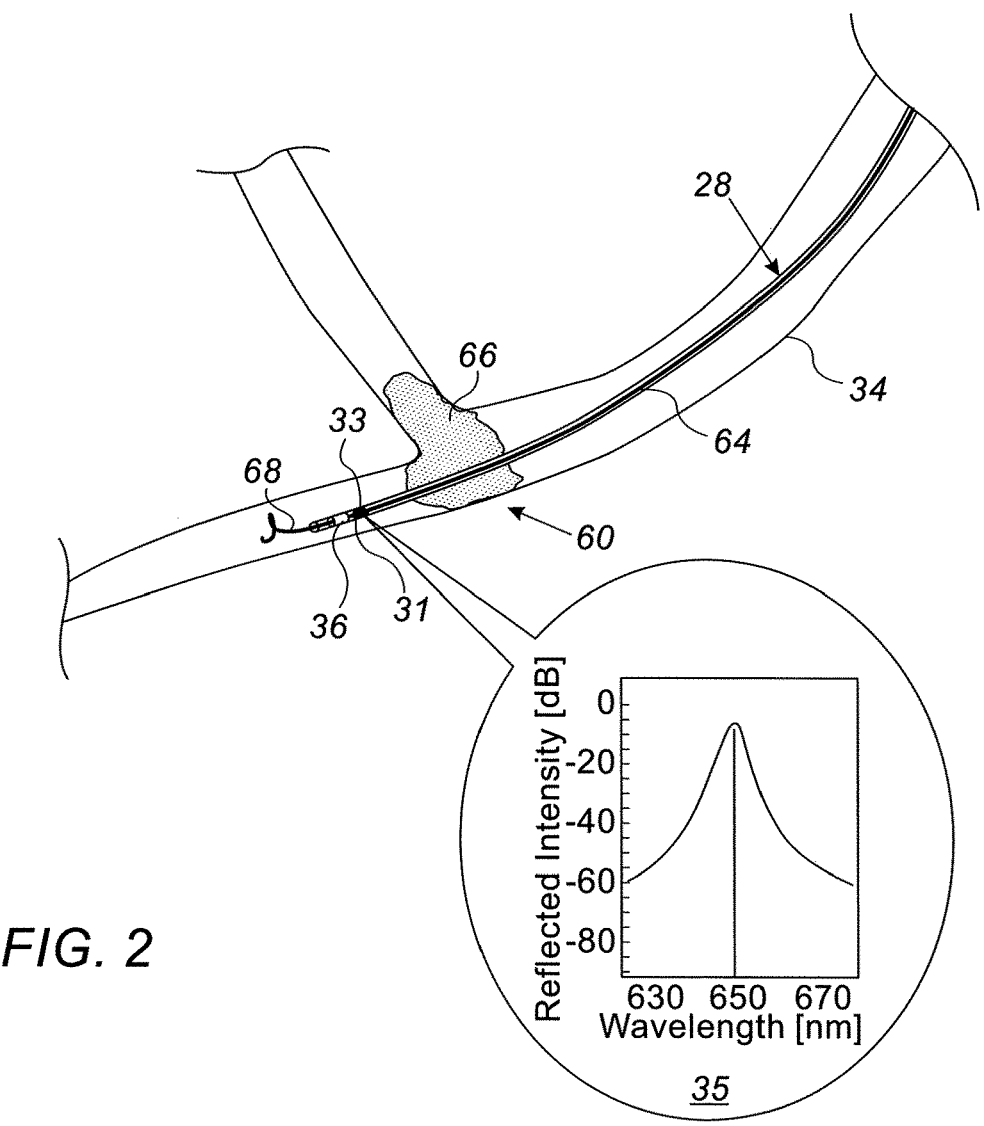
FIG. 2 is a schematic cross-sectional view of a brain clot and a catheter, in accordance with an embodiment of the present invention.

Brain Clot Characterization, and Corresponding Stent Selection, Based on Optical Signal Analysis FIG. 2 is a schematic cross-sectional view of a brain clot 66 and a catheter 28, in accordance with an embodiment of the present invention. As seen, clot 66 blocks blood flow in an artery 34. In some embodiments, physician 54 navigates and advances catheter 28 distally in artery 34, to a location beyond clot 66. As seen in FIG. 2, a distal end 31 of catheter 28 comprises a magnetic position sensor 36, which is used for tracking distal end 31 in the brain to navigate distal end 31 to clot 66. As described above, a system and method for tracking to, and engaging with (e.g., penetrating or traversing), clot 66 are described in the above referenced U.S. Provisional Patent Application 62/675,952.

In some embodiments, catheter 28 comprises an optical fiber 64 to guide an optical signal. Electrooptical measurement unit 55 (shown in FIGS. 1A and 1B) couples the proximal edge of fiber 64, and collects and measures the diagnostic optical signal outputted from fiber 64, and further conveys the measured signal to processor 40. The processor analyzes the conveyed measured signals to identify the composition of clot 66.

In an embodiment, an optical band-stop filter in the form of a Bragg grating 33 is patterned on distal end 31 of fiber 64. A Bragg grating filter reflects light within a given bandwidth about a given center wavelength. In an embodiment, Bragg grating 33 is configured to have its center reflection at a wavelength of 650 nm, as seen in an inset 35, in an exemplary optical reflection characteristic curve of filter 33. Using filter 33, an incident light at 650 nm that traverses clot 66 is reflected and hence double-passes clot 66. Double-passing typically enhances a diagnostic optical signal. For example, it squares an optical attenuation signal relative to that achieved with a single pass.

In another embodiment, fiber 64 is tapered at its distal end, which increases the amplitude of electromagnetic fields that penetrate clot 66, so as to increase the level of the diagnostic optical signal. For example, fiber 64 may have its cladding partially removed from the fiber core at a distal end of the fiber so as to increase a light attenuation signal at 650 nm caused by clot 66. In another embodiment, fiber 64 comprises two optical fibers, wherein one fiber illuminates light and a second fiber collects a transmitted optical signal indicative of the composition of clot 66.

In an embodiment, a clot removal device, such as stent 68, is fitted at distal end 31 of catheter 28. Stent 68 may be used for removing the clot, for example, if a clot composition measurement and analysis, using electrooptical measurement unit 55 and processor 40, respectively, confirms that stent 68 is suitable for handling the identified clot. In case that the optical measurement and subsequent analysis indicate that stent 68 is not optimally suited for the removal of clot 66, a different catheter may then be inserted into clotted blood vessel 34, which, for example, is fitted with a more suitable stent, or another treatment device, based on the evaluation, by physician 54, of the indication received from processor 40 based on the optical signals measured by electrooptical measurement unit 55.

The example illustration shown in FIG. 2 is chosen purely for the sake of conceptual clarity. Fiber 64 may be processed and/or fitted with other or additional optical elements. For example, the fiber may be coated at its end with a reflective layer, such as metal, so as to reflect a wideband optical signal. Other types of optical sensors may be used to determine composition of clot 66, such as ones based, for example, on the generation and/or manipulation of nonlinear optical signals. Other optical configurations may be employed to increase the strength or sensitivity of the diagnostic optical signal. For example, a miniature interferometer may be fitted at distal end 31 or patterned onto fiber 64.

Figure 3:
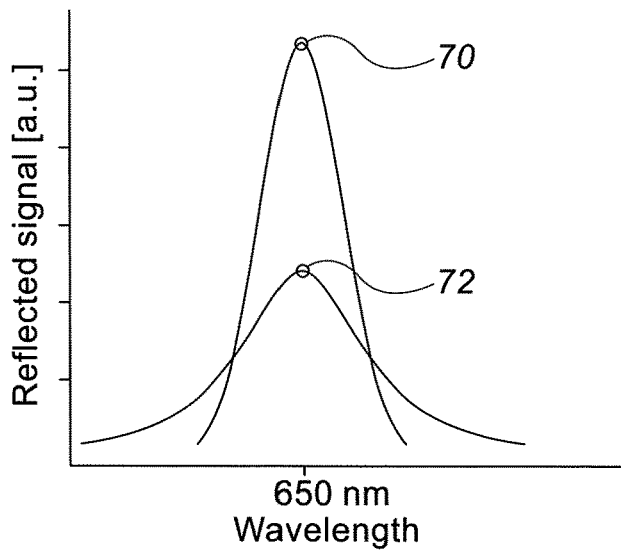
FIG. 3 is a schematic graph showing two optical reflection curves, each indicative of a distinct clot composition, in accordance with an embodiment of the present invention.

FIG. 3 is a schematic graph showing two optical reflection curves, each indicative of distinct clot composition, in accordance with an embodiment of the present invention. The curves exemplify different measured reflected intensities of red light at a wavelength of 650 nm, after double-passing clot 66 using Bragg grating 33. For example, a detector incorporated in electrooptical measurement unit 55 may generate the illustrated signals.

As shown, a signal 70 has a high peak level of reflected intensity at the wavelength of 650 nm. Such a strong reflection signal is indicative of a preponderance of red blood cells in clot 66, since red blood cells have a particularly low absorption of red light at 650 nm.

On the other hand, a low peak level of reflected intensity of signal 72 at wavelength of 650 nm is indicative of a clot having a preponderance of white blood cells, since these absorb all colors similarly, and in particular readily absorb light at a wavelength of 650 nm.

In an embodiment, a threshold value is provided such that a measured reflection intensity above a threshold value indicates a red blood cell clot, while a measured reflection intensity below a threshold value indicates a white blood cell clot.

The example in illustration in FIG. 3 is brought for the sake of conceptual clarity. Specifically, using monochromatic illumination at a wavelength of 650 nm is brought by way of example. Signals at other wavelengths may be used to identify the composition of clot 66.

In some embodiments, electrooptical measurement unit 55 detects a first signal and, after processor 40 analyzes the detected signal, the processor indicates to physician 54 that clot 66 is characterized by white blood cells (i.e., being a white blood cell type of clot). In other embodiments, electrooptical measurement unit 55 detects a second signal, different from the first signal, and correspondingly processor 40 indicates to physician 54 that clot 66 is characterized by red blood cells (i.e., being a red blood cell type of clot).

In an embodiment, electrooptical measurement unit 55 comprises a wideband optical light source and a spectrometer in order for unit 55 to perform a spectral measurement of the wideband optical signal after it interacts with the composition of clot 66. Alternatively or additionally, a spectroscopic measurement may use one or more optical filters fitted with fiber 64. A transmission spectrum of a wideband light, such as white light, may show in spectroscopy, for example, a characteristic notch at blue-green wavelengths due to absorption by red blood cells. A more uniform transmission spectrum would be detected when there is a preponderance of white blood cells in a clot. In some cases, the transmission spectrum of white light would show a characteristic notch at yellow wavelengths due to absorption by less oxygenated red blood cells, as expected in a clot with older red blood cells.

Figure 4:
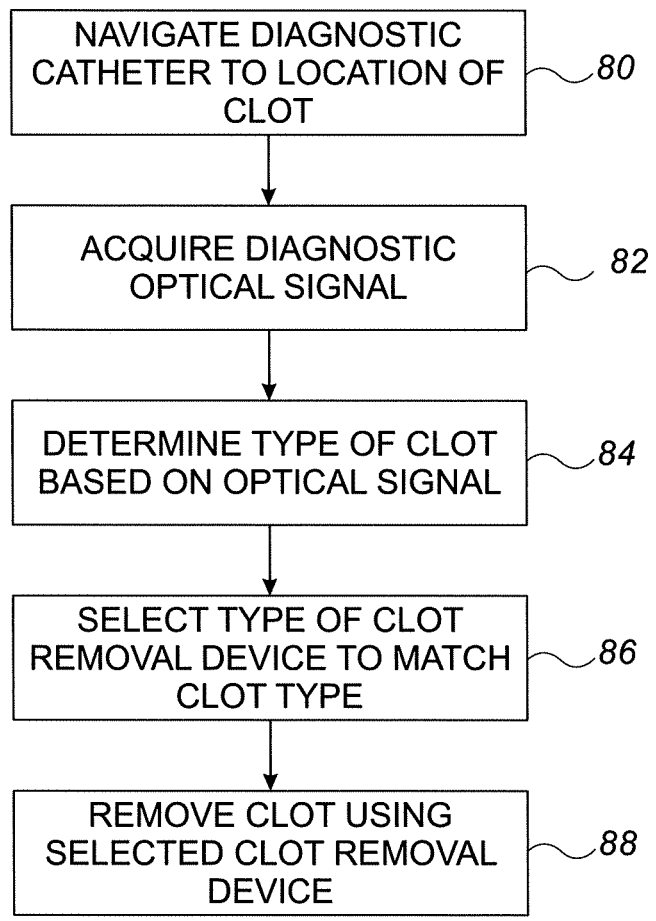
FIG. 4 is a flow chart that schematically illustrates a method for clot composition analysis, and subsequent stent selection and clot removal, in accordance with an embodiment of the present invention.

FIG. 4 is a flow chart that schematically illustrates a method for clot composition analysis, and subsequent stent selection and clot removal, in accordance with an embodiment of the present invention. The process begins with physician 54 navigating catheter 28 to traverse clot 66 with the catheter distal end, at a navigation step 80. Next, physician 54 operates an optical sensing system, comprising an optical device, to measure an optical signal indicative of clot 66 composition, at a signal acquisition step 82.

In an embodiment, the optical device comprises Bragg band stop filter 33, fitted at distal end 31 of fiber optic 64. Bragg band stop filter 33 reflects signals, such as light at 650 nm, indicative of the composition of clot 66. Electrooptical measurement unit 55 measures the 650 nm signals received through fiber 64, and processor 40 analyzes the measured signals, so as to identify the composition of clot 66 (i.e., type of clot), at a clot analysis step 84.

Next, based on the identified composition of clot 66, which processor 40 may present to physician 54 on display 56, physician 54 selects the best suited clot removal device (e.g., stent 68) to use for removing clot 66 from the brain of patient 32, at a removal device selection step 86. Finally, physician 54 removes clot 66 using the selected brain-clot removal device, at a clot removal step 88.

The example flow chart shown in FIG. 4 is chosen purely for the sake of conceptual clarity. In alternative embodiments, for example, based on the indication from processor 40, physician 54 may choose to remove the device by infusing medications at the blood clot site.

Although the embodiments described herein mainly address cerebrovascular applications, the methods and systems described herein can also be used in other applications, such as in biopsy, cancer detection and tissue characterization, for example.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical system, comprising:
a probe for insertion into a blood vessel of a brain, the probe comprising one or more optical fibers configured to guide an optical signal to interact with a brain clot in the blood vessel, and to output the optical signal that interacted with the brain clot;
an electrooptical measurement unit, configured to collect and measure the outputted optical signal to produce a measured optical signal; and
a processor, configured to identify a composition of the brain clot by analyzing the measured optical signal from the probe;
wherein the processor is configured to identify, based on the measured optical signal, whether the composition of the brain clot is characterized by a preponderance of red blood cells or by white blood cells; and
wherein the processor is configured to output a recommendation, based on whether the composition of the brain clot is characterized by the preponderance of red blood cells or by white blood cells, for selecting a brain-clot removal device that matches the composition of the brain clot.

2. The medical system according to claim 1, wherein the processor is configured to identify the composition of the brain clot based on an intensity of the measured optical signal.

3. The medical system according to claim 1, wherein the optical signal comprises monochromatic red light.

4. The medical system according to claim 1, further comprising an optical sensor fitted at a distal end of at least one of the one or more optical fibers.

5. The medical system according to claim 4, wherein the optical sensor comprises a Bragg grating sensor configured to reflect a monochromatic red light.

6. The medical system according to claim 1, wherein the one or more optical fibers guide the optical signal to be transmitted via the brain clot, or to be reflected from the brain clot.

7. The medical system according to claim 1, further comprising a clot removal device fitted at a distal end of the probe.

8. A method, comprising:
guiding an optical signal via one or more optical fibers in a probe that is inserted into a blood vessel of a brain, to interact with a brain clot in the blood vessel;
collecting from the probe and measuring an outputted optical signal that interacted with the brain clot;
identifying a composition of the brain clot via a processor, by analyzing the measured optical signal from the probe and analyzing whether the composition is characterized by a preponderance of red blood cells or by white blood cells;
recommending via the processor a brain-clot removal device that matches the composition of the brain clot;
selecting a brain-clot removal device based on the identified composition of the clot and recommendation via the processor; and
removing the clot using the selected brain-clot removal device.

9. The method according to claim 8, wherein identifying the composition of the brain clot comprises identifying the composition of the brain clot based on an intensity of the optical signal.

10. The method according to claim 8, wherein collecting the outputted optical signal comprises collecting an outputted monochromatic red light.

11. The method according to claim 8, wherein collecting the outputted optical signal comprises collecting the optical signal outputted from an optical sensor fitted at a distal end of at least one of the one or more optical fibers.

12. The method according to claim 11, wherein collecting the optical signal outputted from the optical sensor comprises collecting monochromatic red light reflected by a Bragg grating sensor.

13. The method according to claim 8, wherein guiding the optical signal comprises transmitting the optical signal to the brain clot, or reflecting the optical signal from the brain clot.

* * * * *